United States Patent [19]

Kreighbaum

[11] B 4,001,229

[45] Jan. 4, 1977

[54] ALKANESULFONAMIDO TRIPHENYLETHYLENES

[75] Inventor: William E. Kreighbaum, Evansville, Ind.

[73] Assignee: Mead Johnson & Company, Evansville, Ind.

[22] Filed: Apr. 4, 1974

[21] Appl. No.: 457,931

[44] Published under the second Trial Voluntary Protest Program on March 16, 1976 as document No. B 457,931.

[52] U.S. Cl. .................... 260/247.1 R; 260/239 B; 260/239 E; 260/243 B; 260/240 CA; 260/293.73; 260/326.5 SF; 260/326.82; 260/556 A; 424/246; 424/248.5; 424/267; 424/274; 424/321

[51] Int. Cl.² ...................................... C07D 295/14

[58] Field of Search ... 260/240 CA, 556 A, 247.1 R, 260/293.73, 326.82, 239 E, 239 B, 243 B, 326.5 SF Primary Examiner—Lorraine A. Weinberger
Assistant Examiner—Michael Shippen
Attorney, Agent, or Firm—R. E. Carnahan; R. H. Uloth

[57] ABSTRACT

Triphenylethylenes having an N-(dialkylaminoalkyl)alkanesulfonamide substituent in the one of the phenyl rings may be prepared from similarly substituted benzophenones by reaction thereof with a benzyl Grignard reagent followed by dehydration of the resulting triphenylethanol intermediate and if desired chlorination or nitration of the resulting product. The triphenylethylenes have estrogenic and post-coital antifertility action and are useful as intermediates for the preparation of other triphenylethylene compounds.

12 Claims, No Drawings

ALKANESULFONAMIDO TRIPHENYLETHYLENES

FIELD OF THE INVENTION

This invention concerns carbon compounds of the carbocyclic series bearing an aliphatic sulfonamide substituent. More precisely, they are N-(dialkylaminoalkyl)alkanesulfonanilides in which the sulfonanilide ring is part of a triphenylethylene configuration.

DESCRIPTION OF THE PRIOR ART

The technical and patent literature dealing with the chemistry of carbon compounds of the carbocyclic type and particularly aromatic amines containing a non-nuclear amino group includes a fairly compact class of triphenylethylenes bearing various substituents on the phenyl rings and on the ethylene carbon atom. The compounds have been of interest as estrogenic agents related in action to diethylstilbestrol. Preferred compounds of this class include substances with a tert.-aminoalkyl side chain or a tert.-aminoalkoxy substituent on one of the phenyl rings. Representative patents and publications illustrating this prior art are listed below. The prior art has not, however, provided compounds of the present type in which one of the phenyl groups of a triphenylethylene structure bears an N-substituted alkanesulfonamido group.

Elpern, U.S. Pat. NO. 3,010,965, Nov. 28, 1961.
Palopoli, et al. U.S. Pat. No. 3,244,705, Apr. 5, 1966.
De Wald, U.S. Pat. No. 3,272,841, Sept. 13, 1966.
Harper, et al. Nature, page 87, Oct. 1, 1966.
Collins, et al., J. Med. Chem., 14, 952–7 (1971).
Middleton, U.S. Pat. No. 3,712,929, Jan. 23, 1973.

Elpern discloses triphenylethylenes having a tert.-aminomethyl group on the ethylene carbon atom which substances have coronary dilator activity. Palopoli discloses triphenylethylenes having a tert.-aminoalkyl group on one of the phenyl rings and a chlorine atom on the ethylene carbon atom which substances are used in the treatment of gynecological abnormalities. De Wald discloses triphenylethylenes having a tert.-aminoalkoxy group on one of the phenyl rings and a nitro group on the ethylene carbon atom. Harper, et al. discusses the cis and trans isomers of a specific aminoalkoxy substituted triphenylethylene with respect to its biological activity. Collins, et al. disclose a long series of closely related aminoalkoxy substituted triphenylethylenes with respect to their anti-estrogenic and antifertility activity. Middleton discloses triphenylethylenes having a perfluoroalkyl group of up to 3 carbon atoms on one of the ethylene carbon atoms. The latter are disclosed to be antifertility agents.

SUMMARY OF THE INVENTION

The present invention provides compounds having the following structural formula

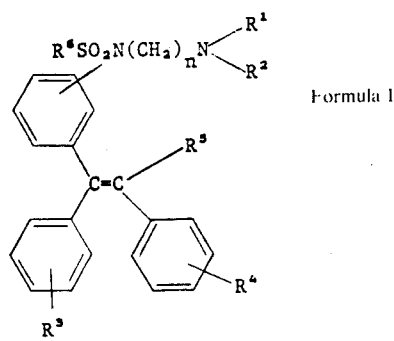

Formula I

In this formula, the phenyl attached $R^3$ and $R^4$ substituents and the sulfonamido group are located in any of the 2, 3, or 4-positions of the respective rings to which they are attached. This is signified in the structural formula by the bond shown from the substituent to the annular space within the respective phenyl ring. $R^1$ and $R^2$ are lower alkyl groups having 1 to 4 carbon atoms and are preferably ethyl groups. They may be methyl, ethyl, propyl, isopropyl, butyl, sec.-butyl, isobutyl or tert.-butyl groups. $R^1$ and $R^2$ may also be joined to form with the nitrogen atom to which they are attached an N-substituted heterocyclic ring having from 3 to 8 annular members and up to 1 additional heteroatom which may be oxygen or sulfur. Examples of such heterocyclic rings are morpholine, thiamorpholine, aziridine, pyrrolidine, piperidine, hexahydroazepine, and octahydroazocine. $R^3$ and $R^4$ are hydrogen, hydroxy, or methoxy. They may be the same or different. $R^5$ is hydrogen, chlorine, bromine, iodine, nitro, alkyl having 1 to 4 carbon atoms or perfluoroalkyl having 1 to 4 carbon atoms. By "perfluoroalkyl" is meant a fluorocarbon group, that is one containing only carbon and fluorine, no hydrogen. $R^6$ is lower alkyl having 1 to 4 carbon atoms and n is the integer 2 or 3 signifying a methylene chain of 2 or 3 carbon atoms between the two nitrogen atoms.

Since the compounds of the present invention are unsymmetrically substituted ethylenes, they exist in two geometric forms, the so-called Z-configuration and the E-configuration. These correspond respectively to what was formerly referred to as the cis and the trans isomers but the Z- and E- denomination is now the generally accepted and uniformly applicable system of nomenclature (J. Am. Chem. Soc., 90, 509 (1968)).

The sulfonamidotriphenylethylenes of the present invention are estrogenic agents and are useful as therapuetic agents where estrogenic action is required, and they are antifertility compounds which are effective by oral or parenteral administration to mammals post-coitally. Their estrogenic activity is manifested in both the rat and the mouse at doses of from 0.5 to 1.0 mg./kg. of body weight orally, but substantially higher doses may be employed since the compounds are relatively non-toxic. Overt signs of side effects, chiefly moderate CNS depression, become apparent only when doses in excess of 250 mg./kg. are administered orally to mice. The acute oral lethal dose (LD$_{50}$) in mice is in excess of 2000 mg./kg. Dosages in the estrogenic range are effective post-coitally when administered following coitus prior to implanation of the fertilized ovum. This period ranges from 0 to 20 days depending upon the species of mammal being treated. In the rat, the antifertility action has been demonstrated by daily dosage on each of the first 6 days following impregnation. The estrogenic activity of the compounds can be demonstrated in either the vaginal cornification or uterotropic assays.

The compounds of the present invention are also useful as intermediates for the preparation of other triphenylethylene derivatives which lack the alkylsulfonyl group and are thus alkylenediamine compounds, that is, triphenylethylenes having an aminoalkylamino group attached to one of the phenyl rings. The latter substances have markedly increased estrogenic and antifertility action and other valuable pharmacological properties.

The compounds of the present invention are bases by virtue of the aliphatic amino side chain. Their basicities are comparable to those of the simple aliphatic amines of analogous structure. They thus form acid addition salts when brought into contact with acids. The salts are prepared by conventional neutralization procedures preferably by contacting the base and the acid in solution in a reaction inert solvent. For medicinal purposes, the pharmaceutically acceptable salts are employed. They are stable at temperatures of storage and use, non-irritating to the skin or mucous membranes, and their toxicities do not differ appreciably from those of the corresponding bases. Examples of pharmaceutically acceptable salts are the citrate, phosphate, nitrate, sulfate, hydrochloride, hydrobromide, mucate, acetate, tartrate, benzoate, etc.

DETAILED DESCRIPTION OF THE INVENTION

The compounds of the present invention are prepared by the Grignard reaction employing a benzophenone of Formula II having the $R^6SO_2N(CH_2)_nNR^1R^2$-substituent in the 2, 3, or 4 position and the $R^3$ substituent in the 2', 3', or 4'-position with the Grignard reagent prepared from an $\alpha$-$R^5$- 2, 3, or 4-$R^4$ substituted benzyl halide (Formula III), or alternatively, by reacting a 2-(2', 3', or 4'-$R^4$-phenyl)-2-$R^5$-alkanoylsulfonanilide of Formula IV with a 2, 3, or 4-substituted $R^3$-phenyl magnesium halide (Formula V) followed in either instance by dehydration of the resulting triphenylethanol. The latter is carried out by warming in solution in the presence of acid. The process is illustrated in the following reaction scheme.

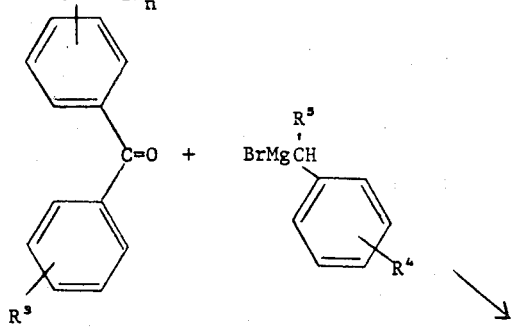

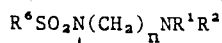    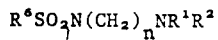

Formula II    Formula III

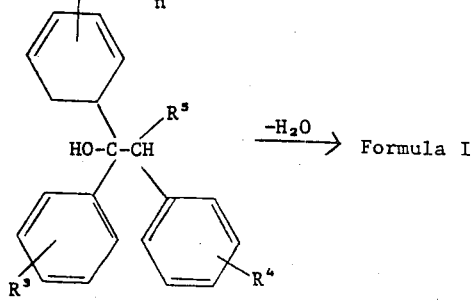

Formula VI

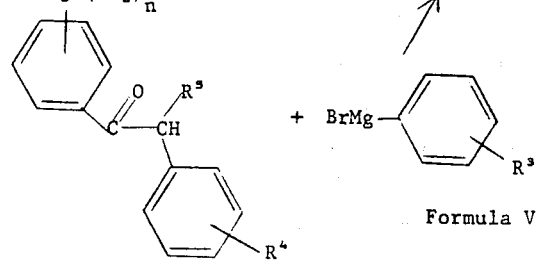    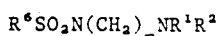

Formula V

Formula IV

The benzophenones of Formula II may be obtained by reaction of 2, 3, or 4-amino-2', 3', or 4'-$R^3$ substituted benzophenone with an $R^6$-sulfonyl halide or anhydride followed by alkylation thereof in the presence of a base such as potassium carbonate with an aminoalkyl halide of the formula $R^1R^2N(CH_2)_nX$ wherein X is Cl, Br, I or other reactive ester group under conditions with which those skilled in the art are acquainted. The phenylalkanoylsulfonanilides of Formula IV are prepared by the ring acylation of an $R^6$-sulfonanilide by an $\alpha$-$R^5$-$\alpha$-toluic acid derivative and N-alkylation of the acylsulfonanilide with an aminoalkyl halide as described with respect to the starting material of Formula II. Preparation of the Grignard reagents of Formulas III and V and reaction thereof with the corresponding ketones of Formulas II and IV to provide the triphenylethanol of Formula VI are carried out according to conditions with which those skilled in the art are acquainted as is the dehydration of the substance of Formula VI to the product of the present invention of Formula I. The substances of Formula I wherein $R^5$ is the perfluoroalkyl group may also be prepared by adaptation of the methods described in the Middleton patent cited above.

DESCRIPTION OF SPECIFIC EMBODIMENTS

Procedure 1. 4'-Benzoylmethanesulfonanilide.

Methanesulfonyl chloride (35.0 g., 0.305 mole) is added dropwise over a 20 min. period with stirring to a solution of 4-aminobenzophenone (60.2 g., 0.305 mole) in 475 ml. of pyridine cooled at 0°–10°C. After the addition is completed, stirring at 0°–10°C. is continued for 4 hrs., and then for an additional 12 hrs. at room temperature. The solution is then heated to 90°C. for 1 hr., allowed to cool, poured into 1.0.1. of water, and then acidified with concentrated hydrochloric acid to pH 1.0. The precipitate which forms is collected on a filter, washed with water, and recrystallized from isopropanol without previous drying to give 70.0 g. (83% yield), m.p. 145–147°C.

Procedure 2. 4'-Benzoylbutanesulfonanilide.

Butanesulfonyl chloride, 0.305 mole, is substitued for methanesulfonyl chloride in the method of Procedure 1; crystallized from benzene-cyclohexane, m.p. 76°–80°C.

Procedures 3-7. Application To Other Aminobenzophenone Starting Materials.

The aminobenzophenones listed below are substituted for 4-aminobenzophenone in the method of Procedure 1 in the same molecular amount to give the correspondingly substituted benzoylmethanesulfonanilides which are also listed below.

(3) 4'-Amino-4-tert.-butoxybenzophenone yields 4'-(4-tert.-butoxybenzoyl)methanesulfonanilide.
(4) 3-Aminobenzophenone yields 3'-benzoylmethanesulfonanilide.
(5) 2-Aminobenzophenone yields 2'-benzoylmethanesulfonanilide.
(6) 4-Amino-2'-methoxybenzophenone yields 4'-(2-methoxybenzoyl)-methanesulfonanilide.
(7) 4-Amino-3'-methoxybenzophenone yields 4'-(3-methoxybenzoyl)-methanesulfonanilide.

Procedure 8.

4'-Benzoyl-N-(2-diethylaminoethyl)methanesulfonanilide.

4'-Benzoylmethanesulfonanilide (69.5 g., 0.252 mole) is dissolved in 1.4 l. of acetonitrile and heated to reflux. Potassium carbonate (35.0 g., 0.253 mole) is added followed by dropwise addition of 2-chlorotriethylamine (34.2 g., 0.252 mole) during 15 min. The reaction mixture is refluxed for 2 hrs. and then kept at room temperature for about 16 hrs. The mixture is filtered and the filtrate concentrated under vacuum. The resulting oil is dissolved in 3N HCl, the acidic solution washed with ethyl ether, and then basified with 50% aqueous NaOH to pH 11.0. The amine which separates is extracted into ethyl ether, and the ether solution is washed first with water, then with saturated sodium chloride, and dried ($MgSO_4$). The ether is removed under reduced pressure to give 89.2 g. (95% yield) of oil which solidifies, m.p. 74°–76°C.

Procedures 9-15. Preparation of Other 4'-Benzoyl-N[$R^1R^2N(CH_2)_n$-]-Substituted Methanesulfonanilides.-

Substitution of the following amino-alkylhalides for 2-chlorotriethylamine in the method of Procedure 8 in the same molecular amount yields the correspondingly N-substituted methanesulfonanilides.

(9) 3-Chloropropyldimethylamine yields 4'-benzoyl-N-(3-dimethylaminoprop-1-yl)methanesulfonanilide.
(10) N-(2-Chloroethyl)morpholine yields 4'-benzoyl-N-[2-(1-morpholinyl)ethyl]methanesulfonanilide.
(11) N-(2-Chloroethyl)piperidine yields 4'-benzoyl-N-[2-(1-piperidyl)ethyl]methanesulfonanilide.
(12) N-(2-Chloroethyl)pyrrolidine yields 4'-benzoyl-N[2-(1-pyrrolidyl)ethyl]methanesulfonanilide.
(13) N-(3-Chloropyropyl)aziridine yields 4'-benzoyl-N-[3-(1-aziridinyl)prop-1-yl]methanesulfonanilide.
(14) N-(2-Chloroethyl)octahydroazocine yields 4'-benzoyl-N[2-(1-hexahydroazocinyl)ethyl]methanesulfonanilide.
(15) Dibutyl-2-chloroethylamine yields 4'-benzoyl-N-(2-dibutylaminoethyl)methanesulfonanilide.

Procedures 16-21. Application To Other Substituted Benzoylalkanesulfonanilides.-

Substitution of the benzoylalkanesulfonanilides listed below in equimolar amount for 4'-benzoylmethanesulfonanilide in Procedure 8 yields the correspondingly substituted benzoyl-N-(2-diethylaminoethyl)alkanesulfonanilides.

(16) 4'-Benzoylbutanesulfonanilide yields 4'-benzoyl-N-(diethylaminoethyl)butanesulfonanilide; citrate salt recrystallized from ethyl acetate-ethanol, m.p. 134.5°–136.0°C.

(17) 4'-(4-tert.-Butoxybenzoyl)methanesulfonanilide yields 4'-(4-tert.-butoxybenzoyl)-N-(diethylaminoethyl)methanesulfonanilide.
(18) 3'-Benzoylmethanesulfonanilide yields 3'-benzoyl-N-(2-diethylaminoethyl)metanesulfonanilide.
(19) 2'-Benzoylmethanesulfonanilide yields 2'-benzoyl-N-(2-diethylaminoethyl)methanesulfonanilide.
(20) 4'-(2-Methoxybenzoyl)methanesulfonanilide yields 4'-(2-methoxybenzoyl)-N-(2-diethylaminoethyl)methanesulfonanilide.
(21) 4'-(3-Methoxybenzoyl)methanesulfonanilide yields 4'-(3-methoxybenzoyl)-N-(2-diethylaminoethyl)methanesulfonanilide.

Procedure 22.
N-(2-Diethylaminoethyl)-4'-[1-hydroxy-2-(4-methoxyphenyl)-1-phenylbut-1-yl]methanesulfonanilide.

Magnesium turnings (10.0 g., 0.411 mole) are employed to prepare the Grignard reagent from 0.333 mole of p-(1-bromopropyl)anisole in 500 ml. of tetrahydrofuran which has been previously dried by distillation for lithium aluminum hydride. The Grignard reaction is initiated by adding a small portion of the p-(1-bromopropyl)anisole to a small portion of the magnesium turnings in a beaker and when the reaction commences as evidenced by a rise in temperature of the mixture it is transferred to the main reaction flask containing the remaining magnesium turnings and tetrahydrofuran solvent. A nitrogen atmosphere is maintained over the reaction mixture which is cooled at 0°–5°C. The main portion of the p-(1-bromopropyl)anisole dissolved in 700 ml. of similarly dried tetrahydrofuran is then added dropwise to the reaction flask during a period of 30 min. The mixture is then agitated overnight (16 hr.) with cooling and then employed for reaction in the same flask with the substituted benzoylmethanesulfonanilide reactant. 4'-Benzoyl-N-(2-diethylaminoethyl)methanesulfonanilide (25.0 g., 0.0667 mole) dissolved in 200 ml. of dried tetrahydrofuran is added dropwise during 45 min. to the reaction mixture with cooling and stirring which is continued for 24 hr. after the material has been added. The reaction product is then recovered by removing the excess magnesium by filtration and treatment of the filtrate first with water (18.0 g., 1.00 mole) and then with a solution of 50 g. of ammonium chloride in 500 ml. of water. Stirring is continued for ½ hr. and the organic layer is then separated and concentrated under reduced pressure. The residual oil is dissolved in ether, the solution washed first with water, the with saturated sodium chloride, and dried over magnesium sulfate. Excess hydrogen chloride gas is then introduced into the solution with stirring and the precipitated hydrochloride salt is collected on a filter and washed with ether; yield 35.2 g. (66%), m.p. 75°–140°C.

Procedures 23–26. Application to Other Substituted Benzyl Grignard Reagents.

The method of Procedure 22 is modified by substitution of the following benzyl halides in like molecular amount for p-(1-bromopropyl)anisole to yield various other substituted 4'-[1-hydroxy-1,2-diphenylethyl]methanesulfonanilide.
(23) α-Butylbenzyl bromide yields N-(2-diethylaminoethyl)-4'-[1-hydroxy-1,2-diphenylhex-1-yl]methanesulfonanilide.
(24) p-Methoxybenzyl bromide yields N-(2-diethylaminoethyl)-4'-[1-hydroxy-2-(4-methoxyphenyl)-1-phenylethyl]methanesulfonanilide.
(25) o-Methoxybenzyl bromide yields N-(2-diethylaminoethyl)-4'-[1-hydroxy-2-(2-methoxyphenyl)-1-phenylethyl]methanesulfonanilide.
(26) m-Methoxybenzyl bromide yields N-(2-diethylaminoethyl)-4'-[1-hydroxy-2-(3-methoxyphenyl)-1-phenylethyl]methanesulfonanilide.

Procedures 27–39. Reaction Of The p-(1-Bromopropyl)anisole Grignard Reagent With Various Substituted 4'-Benzoylmethanesulfonanilides.

The following substituted 4'-benzoylmethanesulfonanilides are substituted in equimolar amount for 4'-benzoyl-N-(2-diethylaminoethyl)methanesulfonanilide in the method of Procedure 22 to give the correspondingly substituted 4'-(1-hydroxy-1,2-diphenylbut-1-yl)methanesulfonanilides.
(27) 4'-Benzoyl-N-(3-dimethylaminoprop-1-yl)methanesulfonanilide yields N-(3-dimethylaminoprop-1-yl)-4'-[1-hydroxy-2-(4-methoxyphenyl)-1-phenylbut-1-yl]methanesulfonanilide.
(28) 4'-Benzoyl-N-[2-(1-morpholinyl)ethyl]methanesulfonanilide yields N-[2-(1-morpholinyl)ethyl]-4'-[1-hydroxy-2-(4-methoxyphenyl)-1-phenylbut-1-yl]methanesulfonanilide.
(29) 4'-Benzoyl-N-[2-(1-piperidyl)ethyl]methanesulfonanilide yields N-[2-(1-piperidyl)ethyl]-4'-[1-hydroxy-2-(4-methoxyphenyl)-1-phenylbut-1-yl]methanesulfonanilide.
(30) 4'-Benzoyl-N-[2-(1-pyrrolidyl)ethyl]methanesulfonanilide yields N-[2-(1-pyrrolidyl)ethyl]-4'-[1-hydroxy-2-(4-methoxyphenyl)-1-phenylbut-1-yl]methanesulfonanilide.
(31) 4'-Benzoyl-N-[3-(1-aziridinyl)prop-1-yl]methanesulfonanilide yields N-[3-(1-aziridinyl)prop-1-yl]-4'-[1-hydroxy-2-(4-methoxyphenyl)-1-phenylbut-1-yl]methanesulfonanilide.
(32) 4'Benzoyl-N-[2-(1-hexahydroazocinyl)ethyl]methanesulfonanilide yields N-[2-(1-octahydroazocinyl)ethyl]-4'-[1-hydroxy-2-(4-methoxyphenyl)-1-phenylbut-1-yl]methanesulfonanilide.
(33) 4'-Benzoyl-N-[2-(diethylamino)ethyl]butanesulfonanilide and benzyl magnesium bromide yields N-(2-diethylaminoethyl)-4'-[1,2-diphenyl)-1-hydroxyethyl]butanesulfonanilide; recrystallized, diisopropyl ether, m.p. 92°–94°C. Anal. C, 70.84; H, 7.86; N, 5.50.
(34) 4'-[4-tert.-Butoxybenzoyl]-N-(2-diethylaminoethyl)methanesulfonanilide yields N-(2-diethylaminoethyl)-4'-[1-hydroxy-1-(4-tert.-butoxyphenyl)-2-(4-methoxyphenyl)-1-phenylbut-1-yl]methanesulfonanilide.
(35) 3'-Benzoyl-N-(2-diethylaminoethyl)methanesulfonanilide yields N-(2-diethylaminoethyl)-3'-[1-hydroxy-2-(4-methoxyphenyl)-1-phenylbut-1-yl]methanesulfonanilide.
(36) 4'-Benzoyl-N-(2-dibutylaminoethyl)methanesulfonanilide yields N-(2-dibutylaminoethyl)-4'-[1-hydroxy-2-(4-methoxyphenyl)-1-phenylbut-1-yl]methanesulfonanilide.
(37) 2'-Benzoyl-N-(2-diethylaminoethyl)methanesulfonanilide yields N-(2-diethylaminoethyl)-2'-[1-hydroxy-2-(4-methoxyphenyl)-1-phenylbut-1-yl]methanesulfonanilide.
(38) N-(2-Diethylaminoethyl)-4'-(2-methoxybenzoyl)methanesulfonanilide yields N-(2-diethylaminoethyl)-4'-[1-hydroxy-1-(2-methoxyphenyl)-2-(4-methoxyphenyl)but-1-yl]methanesulfonanilide.

(39) N-(2-Diethylaminoethyl)-4'-(3-methoxybenzoyl)methanesulfonanilide yields N-(2-diethylaminoethyl)-4'-[1-hydroxy-1-(3-methoxyphenyl)-2-(4-methoxyphenylbut-1-yl]methanesulfonanilide.

Procedure 40.
N-(2-Diethylaminoethyl)-4'-[2-(4-methoxyphenyl)-1-phenyl-1-buten-1-yl]methanesulfonanilide.

N-(2-Diethylaminoethyl)-4'-[1-hydroxy-2-(p-methoxyphenyl)-1-phenylbut-1-yl]methanesulfonanilide hydrochloride (34.5 g., 0.0616 mole) is dissolved in 200 ml. of concentrated hydrochloric acid and 200 ml. ethanol and the solution is refluxed for 1 hr. The ethanol is distilled under reduced pressure and the aqueous residue is basified with 50% aqueous NaOH to pH 11.0. The dehydration product is extracted with ethyl ether and the ether solution is washed with water, saturated sodium chloride, and dried (MgSO$_4$). Distillation of the solvent yields 30.5 g. of an oil which is crystallized by dissolving in hot isopropanol and cooling the solution; 23.2 g., (75% yield with both Z and E isomers present in equal amounts), m.p. 120°–130°C.

Procedures 41–57. Dehydration of Other Substituted Triphenylethanols to yield Substituted Alkanesulfonamidotriphenylethylenes.

Intermediates produced in Procedures 23–39 are dehydrated by treatment with concentrated hydrochloric acid according to the method of Procedure 40. The products produced and the intermediates from which they are prepared are listed below.

(41) N-(2-Diethylaminoethyl)-4'-(1,2-diphenyl-1-hexen-1-yl)methanesulfonanilide from 23.
(42) N-(2-Diethylaminoethyl)-4'-(4-methoxy-β-phenylstyryl)methanesulfonanilide from 24.
(43) N-(2-Diethylaminoethyl)-4'-(2-methoxy-β-phenylstyryl)methanesulfonanilide from 25.
(44) N-(2-Diethylaminoethyl)-4'-(3-methoxy-β-phenylstyryl)methanesulfonanilide from 26.
(45) N-(3-Dimethylaminopropyl)-4'-[2-(4-methoxyphenyl)-1-phenyl-1-buten-1-yl]methanesulfonanilide from 27.
(46) N-[2-(1-Morpholinyl)ethyl]-4'-[2-(4-methoxyphenyl)-1-phenyl-1-buten-1-yl]methanesulfonanilide from 28.
(47) N-[2-(1-Piperidyl)ethyl]-4'-[2-(4-methoxyphenyl)-1-phenyl-1-buten-1-yl]methanesulfonanilide from 29.
(48) N-[2-(1-Pyrrolidyl)ethyl]-4'-[2-(4-methoxyphenyl)-1-phenyl-1-buten-1-yl]methanesulfonanilide from 30.
N-[3-(1-Aziridinyl)prop-1-yl]-4'-[2-(4-methoxyphenyl)-1-phenyl-1-buten-1-yl]methanesulfonanilide from 31.
(50) N-[2-(1-Octahydroazocinyl)ethyl]-4'-[2-(4-methoxyphenyl)-1-phenyl-1-buten-1-yl]methanesulfonanilide from 32.
(51) N-(2-Diethylaminoethyl)-4'-[β-phenylstyryl]-butanesulfonanilide from 33; citrate salt, recrystallized from ethyl acetatemethanol, m.p. 90°–93°C. Anal. C, 63.21; H, 6.87; N, 4.10. Ultra violet spectrum λ max (hydrochloride salt in CHCl$_3$): 301 nm, $\epsilon$= 29,000; 242 nm, $\epsilon$= 21,000. Infra red, significant absorption maxima, citrate salt in KBr wafer: $\nu$ (cm$^{-1}$) 2950, 2600, 1720, 1330, 1140, and 700. NMR of the free base in CDCl$_3$; ppm (tetramethylsilane reference), multiplicity, relative area: 1.0, m, 9; 1.5, m, 4; 2.5, q, 6; 3.1, t, 2; 3.9, t, 2; 7.0–7.3, m, 15.

(52) N-(2-Diethylaminoethyl)-4'-[1-(4-hydroxyphenyl)-2-(4-methoxyphenyl)-1-buten-1-yl]methanesulfonanilide from 34.
(53) N-(2-Diethylaminoethyl)-3'-[2-(4-methoxyphenyl)-1-phenyl-1-buten-1-yl]methanesulfonanilide from 35.
(54) N-(2-Dibutylaminoethyl)-4'-[2-(4-methoxyphenyl)-1-phenyl-1-buten-1-yl]methanesulfonanilide from 36.
(55) N-(2-Diethylaminoethyl)-2'-[2-(4-methoxyphenyl)-1-phenyl-1-buten-1-yl]methanesulfonanilide from 37.
(56) N-(2-Diethylaminoethyl)-4'-[1-(2-methoxyphenyl)-2-(4-methoxyphenyl)-1-buten-1-yl]methanesulfonanilide from 38.
(57) N-(2-Diethylaminoethyl)-4'-[1-(3-methoxyphenyl)-2-(4-methoxyphenyl)-1-buten-1-yl]methanesulfonanilide from 39.

Procedure 58.
Z-2-[p-[1-Phenyl-2-(4-methoxyphenyl)-1-buten-1-yl]anilino]triethylamine.

N-(2-Diethylaminoethyl)-4'-[2-(4-methoxyphenyl)-1-phenyl-1-buten-1-yl]methanesulfonanilide (10.0 g., 0.0197 mole) is dissolved in tetrahydrofuran and added to LiAlH$_4$ (1.0 g., 0.0263 mole) in 400 ml. of tetrahydrofuran and the mixture is refluxed for 8 hrs. Any remaining LiAlH$_4$ is then decomposed by the slow addition of water (1.0 ml.) followed by 15% aqueous NaOH (1.0 ml.) and more water (3.0 ml.). Ethyl ether is added and stirring is continued for 30 min. The inorganic solids are removed by filtration. Separation and concentration of the organic solvent phase yields 8.8 g. of an oil comprised of a mixture of the Z- and E-forms of the desired product. The oil is purified by chromatography on alumina (isopropyl ether). Cooling (−80°C.) a pentane solution of the purified oil yields a solid which is a concentrate rich in the Z-isomer but containing some E-isomer. It is crystallized from isopropanol to give 1.0 g. (10% yield), m.p. 87°–88°C.

Anal: C, 81.26; H, 8.44; N, 6.41. Infra red absorption maxima (0.5% in K Br wafer), $\nu$ (cm$^{-1}$): 3395, 2980, 2845, 1613, 1521, 1290, 1251, 1180, 1034, 819, and 708. NMR of the free base dissolved in CDCl$_3$, ppm (tetramethylsilane reference), multiplicity, relative area: 0.90, t, 3; 0.95, t, 6; 2.45, m, 8; 2.95, m, 2; 3.70, s, 3; 4.09, broad singlet, 1; 6.2–7.2, m, 13.

Procedures 59–75. Other Aminoalkylaminotriphenylethylenes From Substituted Methanesulfonanilide Intermediates.

By application of the lithium aluminum hydride reduction and cleavage described in Procedure 58 to the methanesulfonanilides of Procedures 41–57, the following aminoalkylaminotriphenylethylene compounds are prepared. They are usually obtained as a mixture of the Z- and E-isomers which can be separated from one another by chromatography on alumina and purified by crystallization techniques.

(59) 2-[p-(1,2-Diphenyl-1-hexen-1-yl)anilino]triethylamine from 41.
(60) 2-[p-(4-Methoxy-β-phenylstyryl)anilino]triethylamine from 42.

(61) 2-[p-(2-Methoxy-β-phenylstyryl)anilino]triethylamine from 43.
(62) 2-[p-(3-Methoxy-β-phenylstyryl)anilino]triethylamine from 44.
(63) 3-[p-[2-(4-Methoxyphenyl)-1-phenyl-1-buten-1-yl]anilino]-propyldimethylamine from 45.
(64) N-[2-[p-[2-(4-Methoxyphenyl)-1-phenyl-1-buten-1-yl]anilino]ethyl]morpholine from 46.
(65) N-[2-[p-[2-(4-Methoxyphenyl)-1-phenyl-1-buten-1yl]anilino]ethyl]piperidine from 47.
(66) N-[2-[p-[2-(4-Methoxyphenyl)-1-phenyl-1-buten-1-yl]anilino]ethyl]pyrrolidine from 48.
(67) N-[3-[p-[2-(4-Methoxyphenyl)-1-phenyl-1-buten-1-yl]anilino]propyl]aziridine from 49.
(68) N-[2-[p-[2-(4-Methoxyphenyl)-1-phenyl-1-buten-1-yl]anilino]ethyl]octahydroazocine from 50.
(69) 2-[p-(β-Phenylstyryl)anilino]triethylamine from 51.
(70) 2-[p-[1-(4-Hydroxyphenyl)-2-(4-methoxyphenyl)-1-buten-1-yl]anilino]triethylamine from 52. In this instance an extra 0.25 molecular proportion of lithium aluminum hydride is employed due to the presence of the free hydroxyl group which forms a salt therewith.
(71) 2-[m-[2-(4-Methoxyphenyl)-1-phenyl-1-buten-1-yl]anilino]triethylamine from 53.
(72) 2-[p-[2-(4-Methoxyphenyl)-1-phenyl-1-buten-1-yl]anilino]ethyldibutylamine from 54.
(73) 2-[o-[2-(4-Methoxyphenyl)-1-phenyl-1-buten-1-yl]anilino]triethylamine from 55.
(74) 2-[p-[1-(2-Methoxyphenyl)-2-(4-methoxyphenyl)-1-buten-1-yl]anilino]triethylamine from 56.
(75) 2-[p-[1-(3-Methoxyphenyl)-2-(4-methoxyphenyl)-1-buten-1-yl]anilino]triethylamine from 57.

Procedure 76.
4'-(1-Oxo-2-phenylbutyl)methanesulfonanilide.

Methanesulfonanilide (40 g., 0.234 mole) is added over a 10 minute period with stirring to polyphosphoric acid (400 g.) heated to 90°–100°C. Heating and stirring are continued for additional 10 minutes, at which time 2-phenylbutanoic acid (36.0 g., 0.219 mole) is added portionwise during 20 minutes. After heating and stirring for 10 minutes, the solution is poured into water (600 ml.) and ice (400 g.) with stirring. The water is decanted and ethyl ether (200 ml.) is added to the remaining oil with stirring. After cooling in ice water, the product crystallizes and is collected: 18.4 g., m.p. 143°–147°C. Recrystallization from isopropanol yields 15.7 g. (23% yield), m.p. 148°–150°C.

Procedure 77.
N-(2-Diethylaminoethyl)-4'-(1-oxo-2-phenylbutyl)methanesulfonanilide.

4'-(1-Oxo-2-phenylbutyl)methanesulfonanilide (31.7 g., 0.100 mole), potassium carbonate (13.8 g., 0.100 mole), and 2-chlorotriethylamine (13.6 g., 0.100 mole) are mixed together in 1 liter of acetonitrile and refluxed 18 hr. The reaction mixture is clarified by filtration and concentrated under reduced pressure. The residual oil is dissolved in ethyl ether and the product extracted therefrom with 1.5N HCl. The aqueous acid extract is washed with ethyl ether and then basified with 50% NaOH. The organic material which separates is extracted into ethyl ether and the extracts are washed with water and brine, and the solution dried (MgSO$_4$). The ether is evaporated and the solid residue is crystallized from hexane to yield 24.1 g. (58% yield), m.p. 76°–77°C.

Procedure 78.
N-(2-Diethylaminoethyl)-4'-(1-hydroxy-1,2-diphenylbutyl)methanesulfonanilide.

N-(2-Diethylaminoethyl)-4'-(1-oxo-2-phenylbutyl)-methanesulfonanilide (24.0 g., 0.0576 mole) is dissolved in 500 ml. ethyl ether and added dropwise during ½ hr. to a solution of phenylmagnesium bromide (0.145 mole) in 500 ml. ethyl ether. The mixture is heated at reflux for 16 hrs. After cooling to room temperature, 100 g. of ammonium chloride in 400 ml. water is added and the solution is stirred for 15 min. The ether layer is separated and the aqueous layer is extracted with ethyl ether and the combined ether solutions are washed with water followed by 1N HCl. The acidic aqueous wash is washed with ethyl ether and basified with 50% NaOH to pH 11. The product is extracted with ethyl ether and the ether solution is washed with water and dried (MgSO$_4$). Evaporation of the ethyl ether yields 28 g. of product as an oil (100% yield).

Procedure 79.
N-(2-Diethylaminoethyl)-4'-(α-ethyl-β-phenylstyryl)-methanesulfonanilide.

N-(2-Diethylaminoethyl)-4'-(1-hydroxy-1,2-diphenylbutyl)methanesulfonanilide (15.9 g., 0.0321 mole) is dissolved in 500 ml. of ethanol and the solution is saturated with gaseous HCl and refluxed for 2 hrs. After concentrating under reduced pressure sufficient water is added to dissolve the residue which is then basified to pH 11.0 with 50% aqueous NaOH. The product is extracted with ethyl ether. The ether solution is washed with water, dried (MgSO$_4$), and the ether evaporated leaving 15 g. (100% yield) of oily product.

Procedure 80.
Z-2-[p-(1,2-Diphenyl-1-buten-1-yl)anilino]triethylamine.

A portion of the product of Procedure 79 is refluxed with (8.5 g., 0.0178 mole), LiAlH$_4$ (7.1 g.), and 500 ml. tetrahydrofuran for 4 hrs. The excess remaining LiAlH$_4$ is decomposed by the slow addition of water (7.1 ml.) followed by 15% NaOH (7.1 ml.) and more water (21.3 ml.). The mixture is filtered to remove the inorganic solids which are washed with tetrahydrofuran. After concentrating the washes and filtrate to dryness, water is added, and the product is extracted with ethyl ether. The ether extracts are washed with water, brine, and dried (MgSO$_4$). Evaporation of the ether yields 7.0 g. of oil (100%). Recrystallization from isopropanol yields the pure Z-isomer: 0.8 g. (12% yield), m.p. 103°–104°C.

Anal: C, 84.58; H, 8.57; N, 6.99. NMR of the free base dissolved in CDCl$_3$, ppm (tetramethylsilane reference), multiplicity, relative area: 0.91, t, 3; 0.97, t, 6; 2.50, m, 8; 2.99, m, 2; 4.16, broad singlet, 1; 6.65, m, 4; 7.41, m, 10.

Procedure 81.
2-[p-[α-Chloro-4-methoxy-β-phenylstyryl]anilino]triethylamine.

A solution of 1 g. of chlorine in 10 ml. of carbon tetrachloride is added to a solution of 5 g. of 2-[p-(4- methoxy-β-styryl)anilino]triethylamine in 50 ml. of carbon tetrachloride. The mixture is then stirred at room temperature for 30 minutes and refluxed for 1 hr. The solvent is removed by distillation leaving a crystalline residue of 2-[p-[1,2-dichloro-2-(4-methoxyphenyl)-1-phenylethyl]anilino]triethylamine hydrochloride. The latter without purification is heated at 140°C. for 20 min. to yield the hydrochloride salt of the desired product.

Procedure 82.
2-[p-[α-Bromo-4-methoxy-β-phenylstyryl]anilino]triethylamine.

This substance is prepared by the method of Procedure 81 by substituting bromine in like molecular amount for the chlorine used in that example.

Procedure 83.
2-[p-[α-Iodo-4-methoxy-β-phenylstyryl]anilino]triethylamine.

This substance is made by the method of Procedure 81 by substituting iodine for the chlorine used in that example in like molecular amount.

Procedure 84.
N-(2-Diethylaminoethyl)-4'-[4-methoxy-β-phenylstyryl]acetanilide.

Acetyl chloride (24.0 g., 0.305 mole) is added dropwise during a 20 min. period with stirring to a solution of 2-[p-[2-(4-methoxyphenyl)-1-phenylethenyl]anilino]triethylamine (122 g., 0.3 mole) in 950 ml. of pyridine cooled at 0°–10°C. After the addition is completed, stirring is continued at this temperature for 4 hrs. and then for an additional 12 hr. at room temperature. The solution is heated to 90°C. for 1 hr., allowed to cool, poured into 1.5 l. of water, and then acidified with concentrated hydrochloric acid to pH 1.0. The precipitate which forms is collected on a filter, washed with water, dried and used in the following procedure.

Procedure 85.
N-(2-Diethylaminoethyl)-4'-[4-methoxy-α-nitro-β-phenylstyryl]acetanilide.

The product of Procedure 84, 10 g., is dissolved in 10 ml. of acetic anhydride and added carefully to a solution of 4.5 g. of 70% nitric acid to which 2 drops of concentrated sulfuric acid has been added. The nitric acid-sulfuric acid mixture is prepared with cooling to −15°C. The mixture containing the product is then poured into 150 ml. of water and allowed to stand until the excess acetic anhydride has been hydrolyzed. It is then basified to pH 10.5 and extracted with chloroform. The chloroform extract is dried over magnesium sulfate, the solvent evaporated under reduced pressure, and the residue heated at 90°–100°C. with 30 ml. of 85% phosphoric acid for 1 hr. The dark solution is poured into water, basified, and the product extracted with chloroform. The product is recovered from the chloroform extract after drying by evaporation under reduced pressure.

Procedure 86.
2-[p-[4-Methoxy-α-nitro-β-phenylstyryl]-anilino]triethylamine.

The product of Procedure 85 is dissolved in 95% aqueous ethanol containing about 10% by weight of sodium hydroxide. The solution is heated at reflux for 2 hrs., concentrated to approximately one-third its original volume, and the precipitate collected and washed on the filter several times with water. The resulting product is purified by recrystallization from a suitable solvent.

Procedure 87.
N-(2-Diethylaminoethyl)-4'-(α-chloro-β-phenylstyryl)butanesulfonanilide.

N-(2-Diethylaminoethyl)-4'-(β-phenylstyryl)-butanesulfonanilide hydrochloride (10.5 g., 0.02 mole; refer to Procedure 51) is dissolved in a mixture of 300 ml. of carbon tetrachloride and 20 ml. of chloroform. The mixture is stirred and 39 ml. of a carbon tetrachloride solution containing 1.4 g. (0.02 mole) of chlorine is added thereto during 30 min. The mixture is kept at room temperature for an additional 30 min. and then refluxed for 1 hr. Vigorous evolution of hydrogen chloride gas is apparent during this period. The reaction mixture is allowed to cool and then neutralized with 100 ml. of aqueous 5% sodium hydroxide. The organic layer is separated, dried over magnesium sulfate, and the solvent evaporated yielding 11.0 g. of the desired product. The material is purified by chromatography on an alumina column having dimensions 1 inch by 15 inches and eluting sequentially with 1:1 benzene-octane; benzene; benzene-chloroform, and finally with chloroform and collecting the eluate in 20 fractions. Fractions 15–19 are combined and the desired product recovered as the citrate salt, m.p. 65°–70°C.

Anal: C, 60.72; H, 6.65; N, 3.68.

Ultraviolet spectrum λ max (hydrochloride salt in $CHCl_3$): 301 nm, $\epsilon$= 9,800; 243 nm, $\epsilon$= 11,500. Infra red significant absorption maxima, citrate salt in KBr wafer: $\nu$ ($cm^{-1}$) 2950, 2650, 1740, 1350, 1150, 700.

NMR of the free base in $CDCl_3$; ppm (tetramethylsilane), multiplicity, relative area: 1.0, m, 9; 1.5, m, 4; 2.5, q, 6; 3.1, t, 2; 3.9, t, 2; 7.0–7.3, m, 14.

Procedure 88.
N-(2-Diethylaminoethyl)-4'-(α-nitro-β-phenylstyryl)-butanesulfonanilide.

The nitration method described in Procedure 85 is used to nitrate N-(2-diethylaminoethyl)-4'-(β-phenylstyryl)butanesulfonanilide to give this product.

Procedure 89.
N-[2-[p-[2-(4-Methoxyphenyl-1-phenyl-1-buten-1-yl]anilino]ethyl]hexahydroazepine.

By substitution of N-(2-chloroethyl)hexahydroazepine for 2-chlorotriethylamine in like molecular amount in the method of Procedure 8 and transformation of the resulting intermediate according to Procedures 22, 40 and 58 in that sequence, this desired product is obtained.

Procedure 90.
N-[2-[p-[2-(4-Methoxyphenyl)-1-phenyl-1-buten-1-yl]anilino]ethyl]thiamorpholine.

By substitution of N-(2-chloroethyl)thiamorpholine for 2-chlorotriethylamine in like molecular amount in the method of Procedure 8 and transformation of the resulting intermediate according to Procedures 22, 40, and 58 in sequence, this desired product is obtained.

Procedure 91.
2-[p-[β-phenyl-α-trifluoromethylstyryl]anilino]triethylamine.

A mixture of 4-nitrobenzophenone hydrazone, 0.1 mole, and yellow mercuric oxide, 0.1 mole, and 100 ml. of pentane is stirred at room temperature for 17 hr. Magnesium sulfate 20 g. is added and the suspension is stirred for 1 hr. and filtered. The filtrate is transferred to a round bottom flask and cooled to 0°C. Perfluorothioacetyl fluoride is then bubbled into the rapidly stirred solution until a purple color of the diazo compound disappears. The solution is stirred at room temperature overnight and 1-fluoro-2-(4-nitrophenyl)-2-phenyl-1-trifluoromethylethylene is recovered from the resulting reaction mixture. A solution of commercial phenyllithium (0.1 mole) is then added dropwise to a like molecular amount of the trifluoroethylene compounds dissolved in 80 ml. of ether which is cooled in an ice bath. The reaction mixture is stirred for 2 hrs. and then mixed with 50 ml. of 10% hydrochloric acid. The ether layer is separated, washed with water, dried over magnesium sulfate, and the solvent removed by evaporation under a stream of nitrogen. Recrystallization of the resulting product yields 1,2-diphenyl-1-(4-nitrophenyl)-2-trifluoromethylethylene. The nitro group is reduced to an amino group with iron and hydrochloric acid and the resulting p-(β-phenyl-α-trifluoromethylstyryl)aniline is converted to the methanesulfonanilide according to Procedure 1 and thence to N-(2-diethylaminoethyl)-4'-(β-phenyl-α-trifluoromethylstyryl)sulfonanilide. The sulfonanilide group is cleaved from the latter according to Procedure 58 to yield the desired product.

What is claimed:

1. A compound selected from the group consisting of bases having the formula

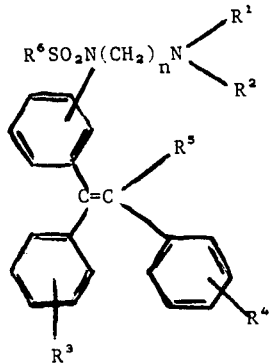

and the pharmaceutically acceptable acid addition salts thereof wherein

R$^1$ and R$^2$ are lower alkyl having 1 to 4 carbon atoms, or together with the nitrogen atom to which they are attached form a heterocyclic ring selected from the group consisting of morpholine, thiamorpholine, aziridine, pyrrolidine, piperidine, hexahydroazepine, and octahydroazocine, R$^3$ and R$^4$ are selected from the group consisting of hydrogen, hydroxy and methoxy, R$^5$ is selected from the group consisting of hydrogen, chlorine, bromine, iodine, nitro, alkyl having 1 to 4 carbon atoms and perfluoroalkyl having 1 to 4 carbon atoms, R$^6$ is lower alkyl having 1 to 4 carbon atoms, and $n$ is the integer 2 or 3.

2. The compound of claim 1 wherein R$^1$, R$^2$ and R$^6$ are lower alkyl having 1 to 4 carbon atoms, R$^3$ and R$^4$ are hydrogen, R$^5$ is chlorine and n is the integer 2.

3. The compound of claim 2, 4'-(α-chloro-β-phenylstyryl)-N-(2-diethylaminoethyl)butanesulfonanilide and the pharmaceutically acceptable acid addition salts thereof.

4. The compound of claim 1 wherein R$^1$, R$^2$ and R$^6$ are lower alkyl having 1 to 4 carbon atoms, R$^3$, R$^4$ and R$^5$ are hydrogen, and n is the integer 2.

5. The compound of claim 4, N-(2-diethylaminoethyl)-4'-(β-phenylstyryl)butanesulfonanilide and the pharmaceutically acceptable acid addition salts thereof.

6. The compound of claim 1 wherein R$^1$, R$^2$, R$^5$, and R$^6$ are lower alkyl having 1 to 4 carbon atoms, R$^3$ and R$^4$ are different and selected from hydrogen and methoxy, and $n$ is the integer 2.

7. The compound of claim 6, N-(2-diethylaminoethyl)-4'-[2-(4-methoxyphenyl)-1-phenyl-1-buten-1-yl]methanesulfonanilide and the pharmaceutically acceptable acid addition salts thereof.

8. The compound of claim 1 wherein R$^1$, R$^2$, R$^5$ and R$^6$ are lower alkyl having 1 to 4 carbon atoms, R$^3$ and R$^4$ are hydrogen and n is the integer 2.

9. The compound of claim 8, N-(2-diethylaminoethyl)-4'-(1,2-diphenyl-1-buten-1-yl)methanesulfonanilide and the pharmaceutically acceptable acid addition salts thereof.

10. The compound of claim 1 wherein R$^1$ and R$^2$ and the nitrogen atom to which they are attached are morpholine, R$^5$ and R$^6$ are lower alkyl having 1 to 4 carbon atoms, and R$^3$ and R$^4$ are different and are selected from hydrogen and methoxy, and $n$ is the integer 2.

11. The compound of claim 1 wherein R$^1$ and R$^2$ and the nitrogen atom to which they are attached are pyrrolidine, R$^5$ and R$^6$ are lower alkyl having 1 to 4 carbon atoms, R$^3$ and R$^4$ are different and selected from hydrogen and methoxy, and n is the integer 2.

12. The compound of claim 1 wherein R$^1$ and R$^2$ and the nitrogen atom to which they are attached are piperidine and R$^5$ and R$^6$ are lower alkyl having 1 to 4 carbon atoms and R$^3$ and R$^4$ are different and selected from hydrogen and methoxy.

* * * * *